(12) United States Patent
Konetzki et al.

(10) Patent No.: US 7,307,076 B2
(45) Date of Patent: Dec. 11, 2007

(54) BETA AGONISTS FOR THE TREATMENT OF RESPIRATORY DISEASES

(75) Inventors: Ingo Konetzki, Warthausen (DE);
Thierry Bouyssou, Warthausen (DE);
Philipp Lustenberger, Basel (CH);
Andreas Schnapp, Biberach (DE);
Marco Santagostino, Mittlebiberach (DE); Christoph Hoenke, Ingelheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/125,890

(22) Filed: May 10, 2005

(65) Prior Publication Data

US 2005/0277632 A1    Dec. 15, 2005

Related U.S. Application Data

(60) Provisional application No. 60/578,528, filed on Jun. 10, 2004.

(30) Foreign Application Priority Data

May 13, 2005    (EP)    ................... 04425342

(51) Int. Cl.
*A61K 31/536* (2006.01)
*A61K 31/4704* (2006.01)
*A61K 31/421* (2006.01)
*C07D 265/36* (2006.01)
*C07D 215/26* (2006.01)
*C07D 263/58* (2006.01)

(52) U.S. Cl. ............... 514/230.5; 514/312; 514/375; 544/105; 546/157; 548/221

(58) Field of Classification Search ............... 548/221; 546/156
See application file for complete search history.

(56) References Cited

U.S. PATENT DOCUMENTS

| | | | |
|---|---|---|---|
| 4,026,897 A * | 5/1977 | Nakagawa et al. | ......... 546/157 |
| 4,223,137 A | 9/1980 | Yoshizaki et al. | |
| 4,460,581 A | 7/1984 | Schromm et al. | |
| 4,579,854 A * | 4/1986 | Iwakuma et al. | ......... 514/312 |
| 4,894,219 A | 1/1990 | Baker et al. | |
| 5,223,614 A | 6/1993 | Schromm et al. | |
| 5,750,701 A * | 5/1998 | Beeley et al. | ......... 546/157 |
| 6,951,888 B2 | 10/2005 | Buettner et al. | |
| 7,056,916 B2 | 6/2006 | Konetzki et al. | |
| 2002/0022625 A1 | 2/2002 | Walland et al. | |
| 2005/0137242 A1 | 6/2005 | Walland | |
| 2005/0222144 A1 | 10/2005 | Konetzki et al. | |

FOREIGN PATENT DOCUMENTS

| | | |
|---|---|---|
| DE | 26 58 544 A | 4/1978 |
| DE | 31 34 590 A1 | 3/1983 |
| EP | 0073505 A1 | 3/1983 |
| EP | 0321864 A2 | 6/1989 |
| JP | 51128982 A2 | 11/1976 |
| JP | 51141880 | 12/1976 |
| JP | 52000283 A2 | 1/1977 |
| WO | WO 2004/016601 A1 | 2/2004 |

OTHER PUBLICATIONS

Milecki et al. Abstract from J. Med. Chem. 1987, 30(9), 1563-6. CAS Abstract Attached.*
Yoshizaki et al. Chemical & Pharmaceutical Bulletin 1978, 26(5), 1611-14.*
Deyrup, M.D. et al: "Structure-Affinity Profile of 8-Hydroxycarbostyril-Bases Agonists that Dissociate Slowly from the Beta2-Adrenoceptor" Naunyn-Schmiedeberg's Arch Pharmacol (1999); vol. 359, #3, pp. 168-177.
Yoshizaki, S., et al.: "Sympathomimetic Amines having a 3,4-Dihydrocarbostyril Nucleus," Chemical & Pharmaceutical bulletin, 26(5), p. 1611-1614, 1978.
Nakagawa, K., et al.: Database Chemabs 'Online! Chemical Abstracts Service, Columbus, Ohio, US, Nov. 10, 1976, p. 1-3.
Yoshizaki, Shiro et al.: "Carbostyril derivatives" Database Chemabs 'Online! Chemical Abstracts Service, Columbus, Ohio, US, Jan. 5, 1977, pp. 1-2.
Nakagawa, K., et al.: "Carbostyril derivatives" Database Chemabs 'Online! Chemical Abstracts Service, Columbus, Ohio, US,, Dec. 7, 1976, pp. 1-2.
Yoshizaki, Shiro et al.: Sympathomimetic Amines Having a Carbostyril Nucleus, Journal of Medicinal Chemistry, 19(9) pp. 1138-1142, 1976.
http://.postgradmed.com/issues/2005/03_05/martinez.htm, downloaded on Nov. 21, 2006.
R. S. Bedi; Indian J. Chest Dis Allied Sci., 2005 47: 243-244.

* cited by examiner

*Primary Examiner*—Rebecca Anderson
*Assistant Examiner*—Jason M Nolan
(74) *Attorney, Agent, or Firm*—Michael P. Morris; Mary-Ellen M. Devlin; Timothy X. Witkowski

(57) ABSTRACT

The present invention relates to compounds of general formula 1 wherein the groups n, A, B, $R^1$, $R^2$ and $R^3$ may have the meanings given in the claims and in the specification, processes for preparing them, and their use as pharmaceutical compositions, particularly as pharmaceutical compositions for the treatment of respiratory complaints.

27 Claims, No Drawings

BETA AGONISTS FOR THE TREATMENT OF RESPIRATORY DISEASES

This application claims priority benefit under 35 USC 119(e) to U.S. Provisional Application 60/578,528, filed Jun. 10, 2004.

The present invention relates to compounds of general formula 1

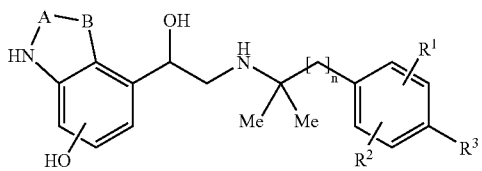

wherein the groups n, A, B, $R^1$, $R^2$ and $R^3$ may have the meanings given in the claims and in the specification, processes for preparing them, and their use as pharmaceutical compositions, particularly as pharmaceutical compositions for the treatment of respiratory complaints.

BACKGROUND TO THE INVENTION

Betamimetics (β-adrenergic substances) are known from the prior art. For example reference may be made in this respect to the disclosure of U.S. Pat. No. 4,460,581, which proposes betamimetics for the treatment of a range of diseases.

For drug treatment of diseases it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the well-being of the patient to a high degree. It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

The aim of the present invention is therefore to provide betamimetics which on the one hand confer a therapeutic benefit in the treatment of respiratory complaints and are also characterised by a longer duration of activity and can thus be used to prepare pharmaceutical compositions with a longer duration of activity. A particular aim of the invention is to prepare betamimetics which, by virtue of their long-lasting effect, can be used to prepare a drug for administration once a day for treating respiratory complaints. A further objective of the invention, apart from those mentioned above, is to prepare betamimetics which are not only exceptionally potent but are also characterised by a high degree of selectivity with respect to the $β_2$-adrenoceptor.

DETAILED DESCRIPTION OF THE INVENTION

Surprisingly it has been found that these opbjectives are achieved with compounds of general formula 1.

Accordingly the present invention relates to compounds of general formula 1

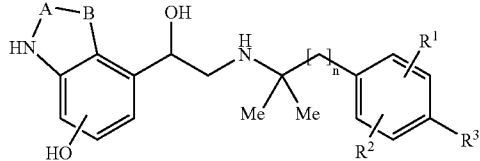

wherein
n denotes 1 or 2, preferably 1;
A denotes a double-bonded group selected from among —(C=O)—, —S(=O)—, —S(=O)$_2$— and —C($R^4R^5$)—;
B denotes a double-bonded group selected from among —O—, —$NR^6$-, —$CH_2$—, —S—$CR^7R^8$—, —$NR^6$—$CR^7R^8$—, —$CH_2$—$CR^7R^8$—, —O—$CR^9R^{10}$— and —CH=CH—;
$R^1$ and $R^2$ which may be identical or different, denote hydrogen, $C_1$-$C_4$-alkyl, halogen, OH or —O—$C_1$-$C_4$-alkyl;
$R^3$ denotes hydrogen, $C_1$-$C_4$-alkyl, OH, halogen, —O—$C_1$-$C_4$-alkyl, —COOH, —COO—$C_1$-$C_4$-alkyl, —O—$C_1$-$C_4$-alkylene-COOH or —O—$C_1$-$C_4$-alkylene-CO—O—$C_1$-$C_4$-alkyl;
$R^4$ and $R^5$ which may be identical or different, denote hydrogen, $C_1$-$C_4$-alkyl, OH, halogen, —O—$C_1$-$C_4$-alkyl, —COOH or —COO—$C_1$-$C_4$-alkyl;
$R^6$ denotes hydrogen or $C_1$-$C_4$-alkyl;
$R^7$ and $R^8$ which may be identical or different, denote hydrogen or $C_1$-$C_4$-alkyl,
$R^9$ and $R^{10}$ which may be identical or different, denote $C_1$-$C_4$-alkyl, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Preferred are compounds of formula 1, wherein
n denotes 1 or 2, preferably 1;
A denotes a double-bonded group selected from among —(C=O)—, —S(=O)$_2$— and —C($R^4R^5$)—;
B denotes a double-bonded group selected from among —O—, —$NR^6$—, —$CH_2$—, —S—$CR^7R^8$—, —$NR^6$—$CR^7R^8$—, —$CH_2$—$CR^7R^8$—, —O—$CR^9R^{10}$— and —CH=CH—;
$R^1$ and $R^2$ which may be identical or different, denote hydrogen, methyl, ethyl, propyl, fluorine, chlorine, bromine, OH, methoxy or ethoxy;
$R^3$ denotes hydrogen, methyl, ethyl, propyl, fluorine, chlorine, bromine, OH, methoxy, ethoxy, —COOH, —COOmethyl, —COOethyl, —O—$CH_2$—COOH, —O—$CH_2$—COO-methyl, —O—$CH_2$—COO-ethyl, —O—$CH_2$—$CH_2$—COOH, —O—$CH_2$—$CH_2$—COO-methyl, —O—$CH_2$—$CH_2$—COO-ethyl, —O—$CH_2$—$CH_2$—$CH_2$—COOH, —O—$CH_2$—$CH_2$—$CH_2$—COO-methyl or —O—$CH_2$—$CH_2$—$CH_2$—COO-ethyl;
$R^4$ and $R^5$ which may be identical or different, denote hydrogen, methyl, ethyl, OH, fluorine, chlorine, —COOH, —COOmethyl or —COOethyl;
$R^6$ denotes hydrogen, methyl, ethyl or propyl, preferably hydrogen;
$R^7$ and $R^8$ which may be identical or different, denote hydrogen, methyl, ethyl or propyl, $R^9$ and $R^{10}$ which may be identical or different, denote methyl, ethyl or propyl, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Also preferred are compounds of formula 1, wherein n denotes 1 or 2, preferably 1;

A denotes a double-bonded group selected from among —(C=O)—, —S(=O)$_2$— and —C($R^4R^5$)—;

B denotes a double-bonded group selected from among —O—, —NR$^6$—, —CH$_2$—, —S—CR$^7R^8$—, —NR$^6$—CR$^7R^8$—, —CH$_2$—CR$^7R^8$—, —O—CR$^9R^{10}$— and —CH=CH—;

$R^1$ and $R^2$ which may be identical or different, denote hydrogen, methyl, ethyl, fluorine, chlorine, OH, methoxy or ethoxy;

$R^3$ denotes hydrogen, methyl, ethyl, fluorine, chlorine, OH, methoxy, ethoxy, —COOH, —COOmethyl, —COOethyl, —O—CH$_2$—COOH, —O—CH$_2$—COO-methyl, —O—CH$_2$—COO-ethyl, —O—CH$_2$—CH$_2$—COOH, —O—CH$_2$—CH$_2$—COO-methyl or —O—CH$_2$—CH$_2$—COO-ethyl;

$R^4$ and $R^5$ which may be identical or different, denote hydrogen, methyl, ethyl, —COOH, —COOmethyl or —COOethyl;

$R^6$ denotes hydrogen, methyl or ethyl;

$R^7$ and $R^8$ which may be identical or different, denote hydrogen, methyl or ethyl, preferably hydrogen or methyl, $R^9$ and $R^{10}$ which may be identical or different, denote methyl or ethyl, preferably methyl, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Also preferred are compounds of formula 1, wherein n denotes 1 or 2, preferably 1;

A denotes a double-bonded group selected from among —(C=O)—, —S(=O)$_2$— and —C($R^4R^5$)—;

B denotes a double-bonded group selected from among —O—, —NH—, —CH$_2$—, —S—CH$_2$—, —NH—CH$_2$—, —CH$_2$—CH$_2$—, —O—CR$^9R^{10}$— and —CH=CH—;

$R^1$ and $R^2$ which may be identical or different, denote hydrogen, methyl, ethyl, fluorine, chlorine, OH, methoxy or ethoxy;

$R^3$ denotes hydrogen, methyl, ethyl, fluorine, chlorine, OH, methoxy, ethoxy, —COOH, —COOmethyl, —COOethyl, —O—CH$_2$—COOH, —O—CH$_2$—COO-methyl, —O—CH$_2$—COO-ethyl, —O—CH$_2$—CH$_2$—COOH, —O—CH$_2$—CH$_2$—COO-methyl or —O—CH$_2$—CH$_2$—COO-ethyl;

$R^4$ and $R^5$ which may be identical or different, denote hydrogen, methyl, ethyl, —COOH, —COOmethyl or —COOethyl;

$R^9$ and $R^{10}$ which may be identical or different, preferably identical, denote methyl or ethyl, preferably methyl, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Also preferred are compounds of formula 1, wherein n denotes 1 or 2, preferably 1;

A denotes a double-bonded group selected from among —(C=O)— and —S(=O)$_2$—;

B denotes a double-bonded group selected from among —O—, —NH—, —CH$_2$—, —S—CH$_2$—, —NH—CH$_2$—, —CH$_2$—CH$_2$—, —O—CR$^9R^{10}$— and —CH=CH—;

$R^1$ and $R^2$ which may be identical or different, denote hydrogen, methyl, ethyl, fluorine, chlorine, OH, methoxy or ethoxy;

$R^3$ denotes hydrogen, methyl, ethyl, fluorine, chlorine, OH, methoxy, ethoxy, —COOH, —COOmethyl, —COOethyl, —O—CH$_2$—COOH, —O—CH$_2$—COO-methyl, —O—CH$_2$—COO-ethyl, —O—CH$_2$—CH$_2$—COOH, —O—CH$_2$—CH$_2$—COO-methyl or —O—CH$_2$—CH$_2$—COO-ethyl;

$R^9$ and $R^{10}$ which may be identical or different, preferably identical, denote methyl or ethyl, preferably methyl, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Also preferred are compounds of formula 1, wherein $R^1$ and $R^2$ which may be identical or different, denote hydrogen, methyl, ethyl, fluorine, chlorine, OH, methoxy or ethoxy;

$R^3$ denotes hydrogen, and wherein the groups n, A and B may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Also preferred are compounds of formula 1, wherein $R^1$ and $R^2$ which may be identical or different, denote hydrogen, methyl, fluorine, chlorine or methoxy;

$R^3$ denotes hydrogen, methyl, fluorine, chlorine or methoxy, and wherein the groups n, A and B may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Also preferred are compounds of formula 1, wherein $R^3$ denotes methyl, ethyl, fluorine, chlorine, OH, methoxy, ethoxy, —COOH, —COOmethyl, —COOethyl, —O—CH$_2$—COOH, —O—CH$_2$—COOmethyl, —O—CH$_2$—COOethyl, —O—CH$_2$—CH$_2$—COOH, —O—CH$_2$—CH$_2$—COOmethyl or —O—CH$_2$—CH$_2$—COOethyl;

and wherein the groups n, $R^1$, $R^2$, A, B may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Also preferred are compounds of formula 1, wherein $R^3$ denotes methyl, ethyl, OH, methoxy, ethoxy, —O—CH$_2$—COOH, —O—CH$_2$—COOmethyl or —O—CH$_2$—COOethyl, preferably OH, methoxy or ethoxy, and wherein the groups n, $R^1$, $R^2$, A, B may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Compounds of formula 1, wherein A denotes —(C=O)— and B denotes —CH=CH— are characterised by general formula 1a

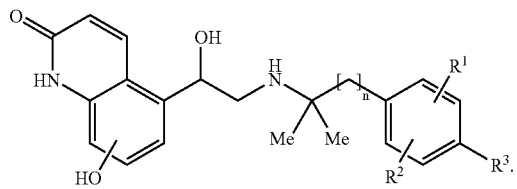

1a

In a preferred aspect the present invention relates to compounds of formula 1a wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Compounds of formula 1, wherein A denotes —(C=O)— and B denotes —$CH_2$—$CH_2$— are characterised by general formula 1b

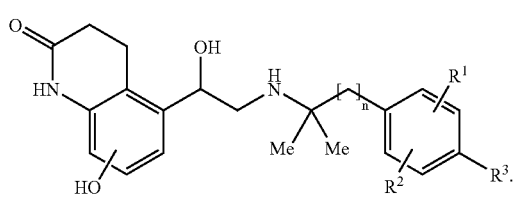

1b

In a preferred aspect the present invention relates to compounds of formula 1b wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Preferred regioisomers of the compounds of formula 1 wherein A denotes —(C=O)— and B denotes —C(methyl)$_2$—O— are characterised by general formula 1c

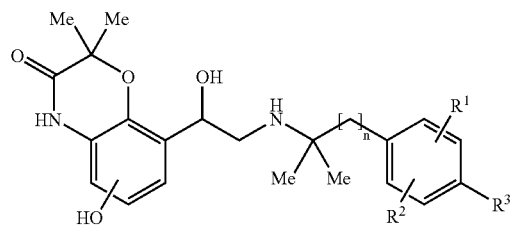

1c

In a preferred aspect the present invention relates to compounds of formula 1c wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Preferred regioisomers of the compounds of formula 1 wherein A denotes —(C=O)— and B denotes —$CH_2$—NH— are characterised by general formula 1d

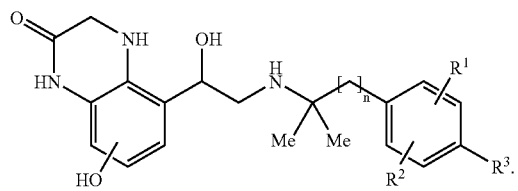

1d

In a preferred aspect the present invention relates to compounds of formula 1d wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Preferred regioisomers of the compounds of formula 1 wherein A denotes —(C=O)— and B denotes —$CH_2$—S— are characterised by general formula 1e

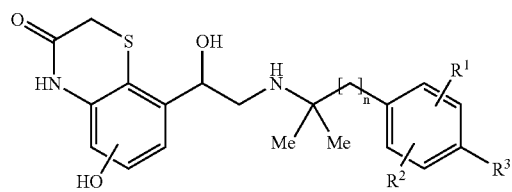

1e

In a preferred aspect the present invention relates to compounds of formula 1e wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Compounds of formula 1 wherein A denotes —(C=O)— and B denotes —NH— are characterised by general formula 1g

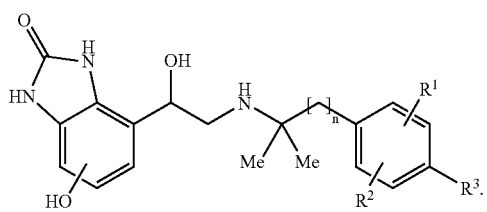

In a preferred aspect the present invention relates to compounds of formula 1g wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Compounds of formula 1 wherein A denotes —(C=O)— and B denotes —O— are characterised by general formula 1h

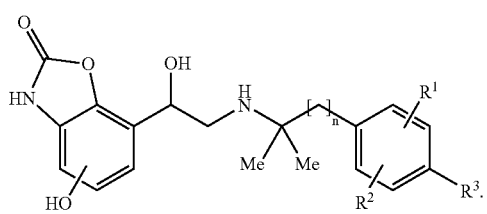

In a preferred aspect the present invention relates to compounds of formula 1h wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Compounds of formula 1 wherein A denotes —$CR^4R^5$— and B denotes —$CH_2$— are characterised by general formula 1i

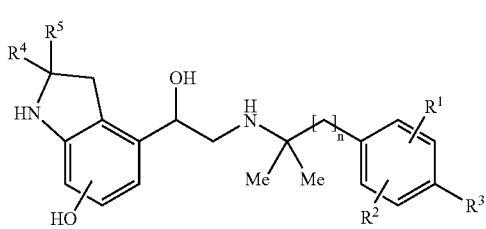

In a preferred aspect the present invention relates to compounds of formula 1i wherein n, $R^1$, $R^2$, $R^3$, $R^4$ and $R^5$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Preferred compounds are those compounds of formula 1i wherein $R^4$ denotes hydrogen and $R^5$ may have one of the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Preferred regioisomers of the compounds of formula 1 wherein A denotes —$SO_2$— and B denotes —$CH_2$—O— are characterised by general formula 1j

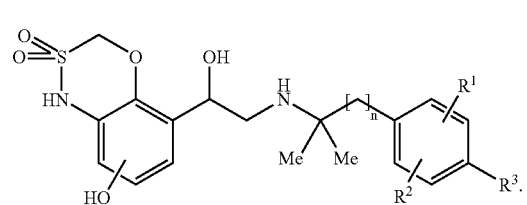

In a preferred aspect the present invention relates to compounds of formula 1j wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

In the compounds of formula 1 the hydroxyl function may be linked to 3 positions of the phenyl ring. Preferred according to the invention are those regioisomers of general formula 1, wherein the hydroxyl function is linked either according to the general formula regio-1

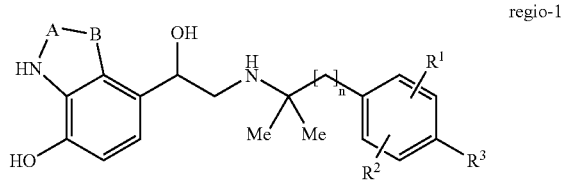

or according to the general formula regio-2

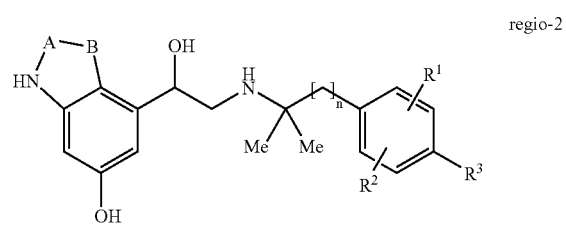

while the groups A, B, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof. Particularly preferred compounds of the present invention are compounds of formula regio-2, while the groups A, B, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Of particular importance are therefore compounds of formula 1a wherein the hydroxyl function is linked according to the general formula regio-2a

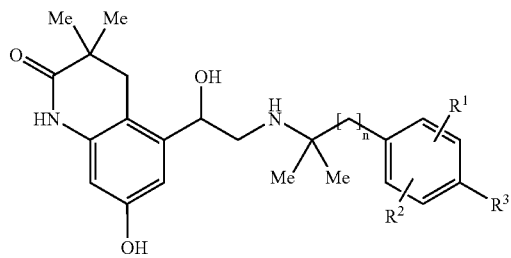

regio-2a and wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Of particular importance are therefore compounds of formula 1b wherein the hydroxyl function is linked according to the general formula regio-2b

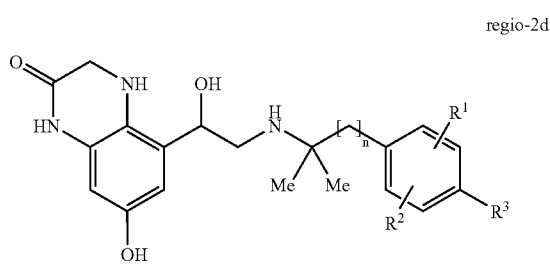

regio-2b and wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Of particular importance are therefore compounds of formula 1c wherein the hydroxyl function is linked according to the general formula regio-2c

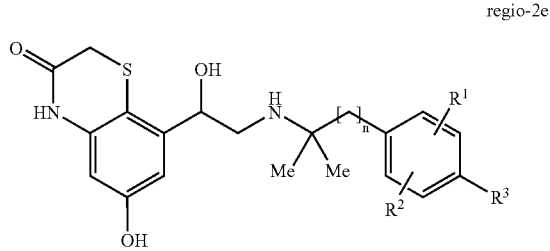

regio-2c and wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Of particular importance are therefore compounds of formula 1d wherein the hydroxyl function is linked according to the general formula regio-2d regio-2d and wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Of particular importance are therefore compounds of formula 1e wherein the hydroxyl function is linked according to the general formula regio-2e regio-2e and wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Of particular importance are therefore compounds of formula 1g wherein the hydroxyl function is linked according to the general formula regio-2g

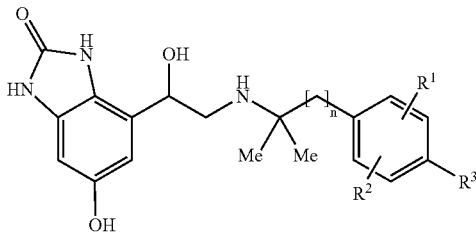

regio-2g and wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Of particular importance are therefore compounds of formula 1h wherein the hydroxyl function is linked according to the general formula regio-2h

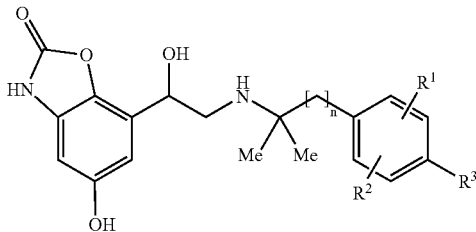

regio-2h and wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Of particular importance are therefore compounds of formula 1i wherein the hydroxyl function is linked according to the general formula regio-2i

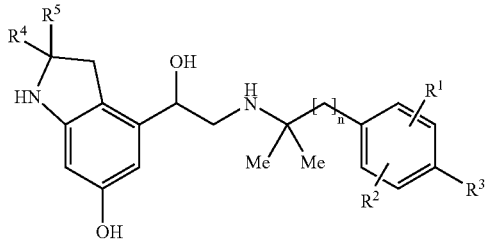

regio-2i and wherein n, $R^1$, $R^2$, $R^4$ and $R^5$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

Of particular importance are therefore compounds of formula 1j wherein the hydroxyl function is linked according to the general formula regio-2j

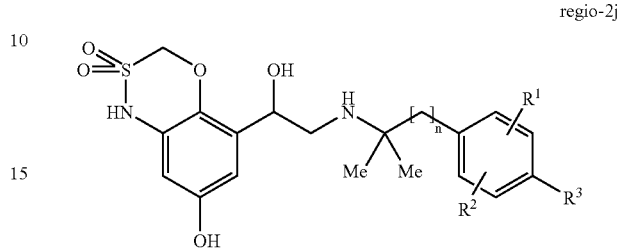

regio-2j and wherein n, $R^1$, $R^2$ and $R^3$ may have the meanings given above, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

In the compounds of formula 1 the groups $R^1$ and $R^2$, if they do not represent hydrogen, may in each case be arranged in the ortho or meta position to the link to the benzylic "—$CH_2$" group. If none of the groups $R^1$ and $R^2$ denotes hydrogen, it is preferable according to the invention to use the compounds of formula 1 wherein either both groups $R^1$ and $R^2$ are in the ortho configuration or both groups $R^1$ and $R^2$ are in the meta configuration, while the use of those compounds wherein both groups $R^1$ and $R^2$ are in the ortho configuration is of particular importance.

In the compounds of formula 1 wherein one of the groups $R^1$ and $R^2$ does not denote hydrogen, this group may be in the ortho or meta configuration relative to the link to the benzylic "—$CH_2$" group. In this case it is particularly preferable according to the invention to use those compounds of formula 1 wherein the group $R^1$ or $R^2$, which does not denote hydrogen, is in the ortho configuration.

Also particularly preferred are compounds of general formula 1 which are selected from among
8-hydroxy-5-{1-hydroxy-2-[2-(4-methoxy-phenyl)-1,1-dimethyl-ethylamino]-ethyl}-1H-quinolin-2-one;
5-{2-[2-(2,4-difluoro-phenyl)-1,1-dimethyl-ethylamino]-1-hydroxy-ethyl}-8-hydroxy-3,4-dihydro-1H-quinolin-2-one;
8-hydroxy-5-{1-hydroxy-2-[2-(4-hydroxy-phenyl)-1,1-dimethyl-ethylamino]-ethyl}-1H-quinolin-2-one;
5-{2-[2-(4-fluoro-phenyl)-1,1-dimethyl-ethylamino]-1-hydroxy-ethyl}-8-hydroxy-3,4-dihydro-1H-quinolin-2-one;
7-hydroxy-5-{1-hydroxy-2-[2-(4-methoxy-phenyl)-1,1-dimethyl-ethylamino]-ethyl}-1H-quinolin-2-one;
5-{2-[2-(3,5-difluoro-phenyl)-1,1-dimethyl-ethylamino]-1-hydroxy-ethyl}-7-hydroxy-1H-quinolin-2-one;
7-hydroxy-5-{1-hydroxy-2-[2-(4-methoxy-phenyl)-1,1-dimethyl-ethylamino]-ethyl}-3,4-dihydro-1H-quinolin-2-one;
5-{2-[2-(4-ethoxy-phenyl)-1,1-dimethyl-ethylamino]-1-hydroxy-ethyl}-7-hydroxy-3,4-dihydro-1H-quinolin-2-one;
4-hydroxy-7-{1-hydroxy-2-[2-(4-methoxy-phenyl)-1,1-dimethyl-ethylamino]-ethyl}-3H-benzoxazol-2-one;
4-hydroxy-7-{1-hydroxy-2-[2-(4-hydroxy-phenyl)-1,1-dimethyl-ethylamino]-ethyl}-3H-benzoxazol-2-one;

5-hydroxy-8-{1-hydroxy-2-[2-(4-hydroxy-phenyl)-1,1-dimethyl-ethylamino]-ethyl}-2,2-dimethyl-4H-benzo[1,4]oxazin-3-one;
5-hydroxy-7-{1-hydroxy-2-[2-(4-methoxy-phenyl)-1,1-dimethyl-ethylamino]-ethyl}-3H-benzoxazol-2-one;
7-{2-[2-(4-ethoxy-phenyl)-1,1-dimethyl-ethylamino]-1-hydroxy-ethyl}-5-hydroxy 3H-benzoxazol-2-one;
6-hydroxy-8-{1-hydroxy-2-[2-(4-methoxy-phenyl)-1,1-dimethyl-ethylamino]-ethyl}-2,2-dimethyl-4H-benzo[1,4]oxazin-3-one;
8-{2-[2-(4-fluoro-phenyl)-1,1-dimethyl-ethylamino]-1-hydroxy-ethyl}-6-hydroxy 2,2-dimethyl-4H-benzo[1,4]oxazin-3-one and
5-hydroxy-8-{1-hydroxy-2-[2-(4-methoxy-phenyl)-1,1-dimethyl-ethylamino]-ethyl}-2,2-dimethyl-4H-benzo[1,4]oxazin-3-one, optionally in the form of the individual enantiomers, mixtures of the individual enantiomers or racemates, optionally in the form of the acid addition salts thereof with pharmacologically acceptable acids as well as optionally in the form of the solvates and/or hydrates thereof.

In another aspect the present invention relates to the above-mentioned new compounds of formula 1 as pharmaceutical compositions. The present invention also relates to the use of the above-mentioned compounds of general formula 1 for preparing a pharmaceutical composition for the treatment of respiratory complaints.

The present invention preferably relates to the use of the above-mentioned compounds of general formula 1 for preparing a pharmaceutical composition for the treatment of respiratory complaints, which are selected from among obstructive pulmonary diseases of various origins, pulmonary emphysema of various origins, restrictive pulmonary diseases, interstitial pulmonary diseases, cystic fibrosis, bronchitis of various origins, bronchiectasis, ARDS (adult respiratory distress syndrome) and all forms of pulmonary oedema.

It is preferable to use compounds of general formula 1 for preparing a pharmaceutical composition for the treatment of obstructive pulmonary diseases which are selected from among COPD (chronic obstructive pulmonary disease), bronchial asthma, paediatric asthma, severe asthma, acute asthma attacks and chronic bronchitis, while it is particularly preferable according to the invention to use them for preparing a pharmaceutical composition for the treatment of bronchial asthma.

It is also preferable to use compounds of general formula 1 for preparing a pharmaceutical composition for the treatment of pulmonary emphysemas that have their origin in COPD (chronic obstructive pulmonary disease) or α1-proteinase inhibitor deficiency.

It is also preferable to use compounds of general formula 1 for preparing a pharmaceutical composition for the treatment of restrictive pulmonary diseases, which are selected from among allergic alveolitis, restrictive pulmonary diseases triggered by work-related noxious substances, such as asbestosis or silicosis, and restriction caused by lung tumours, such as for example lymphangiosis carcinomatosa, bronchoalveolar carcinoma and lymphomas.

It is also preferable to use compounds of general formula 1 for preparing a pharmaceutical composition for the treatment of interstitial pulmonary diseases which are selected from among pneumonia caused by infections, such as for example infection by viruses, bacteria, fungi, protozoa, helminths or other pathogens, pneumonitis caused by various factors, such as for example aspiration and left heart insufficiency, radiation-induced pneumonitis or fibrosis, collagenoses, such as for example lupus erythematodes, systemic sclerodermy or sarcoidosis, granulomatoses, such as for example Boeck's disease, idiopathic interstitial pneumonia or idiopathic pulmonary fibrosis (IPF).

It is also preferable to use compounds of general formula 1 for preparing a pharmaceutical composition for the treatment of cystic fibrosis or mucoviscidosis.

It is also preferable to use compounds of general formula 1 for preparing a pharmaceutical composition for the treatment of bronchitis, such as for example bronchitis caused by bacterial or viral infection, allergic bronchitis and toxic bronchitis.

It is also preferable to use compounds of general formula 1 for preparing a pharmaceutical composition for the treatment of bronchiectasis.

It is also preferable to use compounds of general formula 1 for preparing a pharmaceutical composition for the treatment of ARDS (adult respiratory distress syndrome).

It is also preferable to use compounds of general formula 1 for preparing a pharmaceutical composition for the treatment of pulmonary oedemas, for example toxic pulmonary oedema after aspiration or inhalation of toxic substances and foreign substances.

Particularly preferably, the present invention relates to the use of the compounds of formula 1 for preparing a pharmaceutical composition for the treatment of asthma or COPD. Also of particular importance is the above-mentioned use of compounds of formula 1 for preparing a pharmaceutical composition for once-a-day treatment of inflammatory and obstructive respiratory complaints, particularly for the once-a-day treatment of asthma or COPD.

Moreover the present invention relates to a method of treating the above-mentioned diseases, characterised in that one or more of the above-mentioned compounds of general formula 1 are administered in therapeutically effective amounts. The present invention preferably relates to methods of treating asthma or COPD, characterised in that one or more of the above-mentioned compounds of general formula 1 are administered once a day in therapeutically effective amounts.

In another aspect the present invention relates to the above-mentioned new compounds of formula 1 in the form of the individual optical isomers, mixtures of the individual enantiomers or racemates. Particularly preferred are compounds of formula 1 in the form of the enantiomerically pure compounds, while the R-enantiomers of the compounds of formula 1 are of exceptional importance according to the invention. The R-enantiomers of the compounds of formula 1 may be represented by general formula R-1

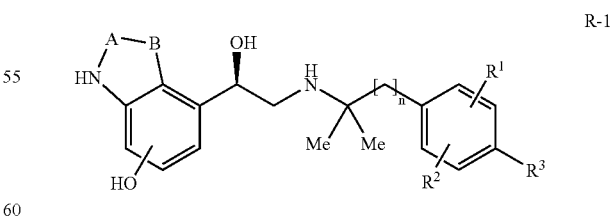

wherein the groups n, A, B, $R^1$, $R^2$ and $R^3$ may have the meanings given above.

Methods for separating racemates into the respective enantiomers are known in the art and may be used to prepare the enantiomerically pure R- or S-enantiomers of the compounds of formula 1 analogously.

In another aspect the present invention relates to the above-mentioned compounds of formula 1 in the form of the acid addition salts thereof with pharmacologically acceptable acids as well as optionally in the form of the solvates and/or hydrates thereof.

By acid addition salts with pharmacologically acceptable acids are meant for example salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate.

Of the above-mentioned acid addition salts the salts of hydrochloric acid, maleic acid and fumaric acid and acetic acid are particularly preferred according to the invention.

Unless otherwise stated, the alkyl groups are straight-chained or branched alkyl groups having 1 to 4 carbon atoms. The following are mentioned by way of example: methyl, ethyl, propyl or butyl. In some cases the abbreviations Me, Et, Prop or Bu are used to denote the groups methyl, ethyl, propyl or butyl. Unless otherwise stated, the definitions propyl and butyl include all the possible isomeric forms of the groups in question. Thus, for example, propyl includes n-propyl and iso-propyl, butyl includes iso-butyl, sec.butyl and tert.-butyl, etc.

Unless otherwise stated, the alkylene groups are branched and unbranched double-bonded alkyl bridges with 1 to 4 carbon atoms. Examples include: methylene, ethylene, n-propylene or n-butylene.

Unless otherwise stated, the alkyloxy groups (O-alkyl or alkoxy groups) are branched and unbranched alkyl groups with 1 to 4 carbon atoms which are linked via an oxygen atom. The following are mentioned by way of example: methyloxy, ethyloxy, propyloxy or butyloxy. In some cases the abbreviations MeO-, EtO-, PropO- or BuO- may be used to denote the methyloxy, ethyloxy, propyloxy or butyloxy groups. Unless otherwise stated, the definitions propyloxy and butyloxy include all the possible isomeric forms of the groups in question. Thus, for example, propyloxy includes n-propyloxy and iso-propyloxy, butyloxy includes iso-butyloxy, sec.butyloxy and tert.-butyloxy, etc. In some cases the term alkoxy may be used instead of alkyloxy within the scope of the present invention. The groups methyloxy, ethyloxy, propyloxy or butyloxy may therefore also be referred to by the names methoxy, ethoxy, propoxy or butoxy.

Halogen within the scope of the present invention denotes fluorine, chlorine, bromine or iodine. Unless stated to the contrary, fluorine, chlorine and bromine are the preferred halogens.

The compounds according to the invention may be prepared analogously to methods already known in the art. Suitable methods of production are known for example from U.S. Pat. No. 4,460,581, which is hereby incorporated by reference at this point.

The Examples that follow serve to illustrate the present invention in more detail without restricting it to the subject-matter described by way of example.

Synthesis of the Intermediates

Intermediate step 1: 5-benzyloxy-7-(2-ethoxy-2-hydroxy-acetyl)-3H-benzoxazol-2-one

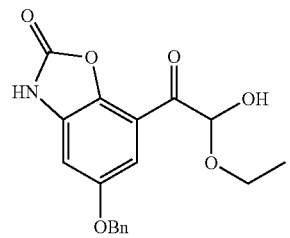

a) 1-(5-benzyloxy-2-hydroxy-3-nitro-phenyl)-ethanone 18 mL fuming nitric acid are added dropwise to a solution of 81.5 g (0.34 mol) 1-(5-benzyloxy-2-hydroxy-phenyl)-ethanone (known from U.S. Pat. No. 4,460,581) in 700 mL acetic acid while being cooled with the ice bath such that the temperature does not exceed 20° C. Then the reaction mixture is stirred for two hours at ambient temperature, poured onto ice water and filtered. The product is recrystallised from isopropanol, suction filtered and washed with isopropanol and diisopropylether. Yield: 69.6 g (72%); mass spectroscopy [M+H]$^+$=288.

b) 1-(3-amino-5-benzyloxy-2-hydroxy-phenyl)-ethanone 69.5 g (242 mmol) 1-(5-benzyloxy-2-hydroxy-3-nitro-phenyl)-ethanone are dissolved in 1.4 L methanol and hydrogenated in the presence of 14 g rhodium on charcoal (10%) as catalyst at 3 bar and ambient temperature. Then the catalyst is filtered off and the filtrate is evaporated down. The residue is reacted further without additional purification.

Yield: 60.0 g (96%), $R_f$ value=0.45 (dichloromethane on silica gel).

c) 7-acetyl-5-benzyloxy-3H-benzoxazol-2-one 52 g (0.53 mol) phosgene are piped into a solution of 121 g (0.47 mol) 1-(3-amino-5-benzyloxy-2-hydroxy-phenyl)-ethanone in 800 mL pyridine at 20 to 40° C. The reaction mixture is heated to 50° C. for 2 hours, then poured onto ice and acidified with conc. hydrochloric acid. A reddish-brown solid is isolated which is repeatedly recrystallised from ethanol with the addition of activated charcoal.

Yield 67.5 g (50.6%); melting range: 163-166° C.

d) 5-benzyloxy-7-(2-ethoxy-2-hydroxy-acetyl)-3H-benzoxazol-2-one 20 g (71 mmol) 7-acetyl-5-benzyloxy-3H-benzoxazol-2-one and 8 g (72 mmol) selenium dioxide are stirred in the presence of activated charcoal in 100 mL dioxane and 3.1 mL water for 8 hours at reflux temperature. The solid is filtered off, the solvent is distilled off and the residue is combined with 50 mL ethanol. The mixture is refluxed for 15 minutes and then filtered through activated charcoal. The solid that precipitates on cooling is suction filtered for 3 hours and washed with ethanol and diethyl ether.

Yield 7 g (29%); melting range: 140-143° C.

Intermediate step 2: 6-benzyloxy-8-(2-ethoxy-2-hydroxy-acetyl)-2,2-dimethyl-4H-benzo[1,4]oxazin-3-one

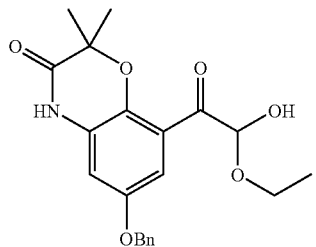

a) N-(3-acetyl-5-benzyloxy-2-hydroxy-phenyl)-2-bromo-2-methyl-propionamide 4.64 g (25 mmol) 2-bromo-2-methyl-propionyl chloride are added dropwise at 5 to 20° C. to a solution of 5.15 g (20 mmol) 1-(3-amino-5-benzyloxy-2-hydroxy-phenyl)-ethanone in 20 mL pyridine. After the addition has ended the mixture is stirred for 15 minutes, combined with ice water and 100 mL ethyl acetate and acidified with conc. hydrochloric acid. The organic phase is separated off, washed with water and dried with sodium sulphate. After the solvent has been distilled off the residue is crystallised from a diethyl ether/petroleum ether mixture.

Yield: 6.8 g (84%); melting range: 88-90° C.

b) 8-acetyl-6-benzyloxy-2,2-dimethyl-4H-benzo[1,4]oxazin-3-one 6.60 g (16.2 mmol) N-(3-acetyl-5-benzyloxy-2-hydroxy-phenyl)-2-bromo-2-methyl-propionamide and 2.76 g (20 mmol) potassium carbonate are stirred for 1 hour in 70 mL acetonitrile at reflux temperature. The solid is suction filtered, the filtrate is evaporated down and the residue is combined with 30 mL ethyl acetate. After further filtration and after the solvent has been distilled off the crude product is recrystallised from a little methanol.

Yield: 1.00 g (19%); mass spectroscopy [M+H]$^+$=326; melting range: 148-150° C.

c) 6-benzyloxy-8-(2-ethoxy-2-hydroxy-acetyl)-2,2-dimethyl-4H-benzo[1,4]oxazin-3-one The compound is prepared analogously to the method described for Intermediate step 1d) from 8-acetyl-6-benzyloxy-2,2-dimethyl-4H-benzo[1,4]oxazin-3-one.

Intermediate step 3: 4-benzyloxy-7-(2-ethoxy-1,2-dihydroxy-ethyl)-3H-benzoxazol-2-one

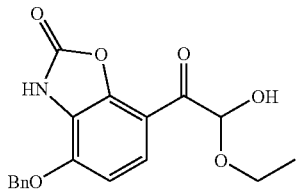

a) 7-acetyl-4-benzyloxy-3H-benzoxazol-2-one 41 mL phenyl chloroformate are added dropwise to a solution of 47 g (183 mmol) 1-(3-amino-4-benzyloxy-2-hydroxy-phenyl)-ethanone (known from U.S. Pat. No. 4,460,581) in 135 mL pyridine, whereupon the temperature rises to 75° C. The mixture is stirred for 4 hours at 90-95° C., poured onto ice and acidified with hydrochloric acid. The precipitated solid is suction filtered, washed with diethyl ether and heated in 500 mL 95% acetonitrile for 30 minutes at reflux temperature. After cooling the solid is filtered off and washed with acetonitrile and diethyl ether.

Yield: 50 g (97%); melting range: 242-244° C.

b) 4-benzyloxy-7-(2-ethoxy-1,2-dihydroxy-ethyl)-3H-benzoxazol-2-one 49.5 g (175 mmol) 7-acetyl-4-benzyloxy-3H-benzoxazol-2-one and 19.6 g (177 mmol) selenium dioxide are refluxed for 8 hours in 200 mL dioxane and 8 mL water in the presence of activated charcoal. The insoluble constituents are suction filtered, the solvent is distilled off and the residue is combined with 150 mL ethanol. The mixture is refluxed for 30 minutes and then filtered through activated charcoal. After the addition of a crystallisation aid the product is precipitated out of the cooled solution. It is suction filtered and washed with ethanol and diethyl ether.

Yield: 30 g (50%); melting range: 153-155° C.

Intermediate step 4: 5-benzyloxy-8-(2-ethoxy-2-hydroxy-acetyl)-2,2-dimethyl-4H-benzo[1,4]oxazin-3-one

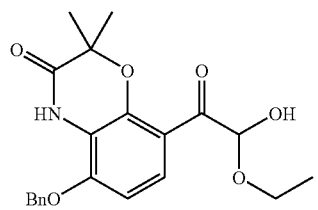

a) 8-acetyl-5-benzyloxy-2,2-dimethyl-4H-benzo[1,4]oxazin-3-one 28 g (0.15 mol) 2-bromo-2-methyl-propionyl chloride are added dropwise to 25.7 g (0.10 mol) 1-(3-amino-4-benzyloxy-2-hydroxy-phenyl)-ethanone and 41 g (0.30 mol) potassium carbonate in 215 mL acetonitrile. After 8 hours stirring at reflux temperature the solid is filtered off, the filtrate is evaporated down and the residue is crystallised from ethanol. Yield: 11.2 g (35%); melting range=124-126° C.

b) 5-benzyloxy-8-(2-ethoxy-2-hydroxy-acetyl)-2,2-dimethyl-4H-benzo[1,4]oxazin-3-one 9.6 g (30 mmol) 8-acetyl-5-benzyloxy-2,2-dimethyl-4H-benzo[1,4]oxazin-3-one, 3.3 g (30 mmol) selenium dioxide and activated charcoal are stirred for 7 hours in 90 mL dioxane and 2 mL water at reflux temperature. The solid is suction filtered, the filtrate is evaporated down and the residue is refluxed for 30 minutes in 100 ml of ethanol. The solvent is distilled off and the residue is dissolved in 125 mL ethyl acetate. It is extracted successively with potassium carbonate solution and water, dried with sodium sulphate and evaporated down. The oil remaining (10.1 g) is further reacted directly.

Intermediate step 5:
8-benzyloxy-5-oxiranyl-1H-quinolin-2-one

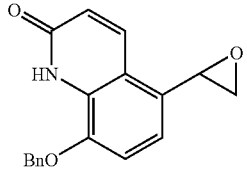

a) 8-benzyloxy-5-(2-chloro-acetyl)-1H-quinolin-2-one 25.2 g (86 mmol) 5-acetyl-8-benzyloxy-1H-quinolin-2-one (European Journal of Medicianl Chemistry 1984, 19(4), 341) and 50 g (142 mmol) benzyltrimethylammonium dichloriodate in 500 mL dichloroethane and 300 mL methanol are stirred overnight at reflux temperature. The reaction mixture is evaporated down and the residue is stirred overnight in THF and 1 N hydrochloric acid. After the THF has been distilled off the precipitated solid is suction filtered, washed with diethyl ether and dried.

Yield: 23.6 g (84%); mass spectroscopy $[M+H]^+=328/30$.

b) 8-benzyloxy-5-(2-chloro-1-hydroxy-ethyl)-1H-quinolin-2-one 238 mL of a 2 molar solution of lithium borohydride in THF are added dropwise to 52 g (159 mmol) 8-benzyloxy-5-(2-chloro-acetyl)-1H-quinolin-2-one in 650 mL THF at 0° C. It is stirred for two hours at 0° C., then heated to ambient temperature, combined with 200 mL dichloromethane and 75 mL water and stirred for a further hour. The precipitated solid is suction filtered and the organic phase of the filtrate is separated off and freed from the solvent. The residue is combined with the solid from the preceding filtration and repeatedly stirred with diethyl ether and THF. Yield: 51.6 g (99%); mass spectroscopy $[M+H]^+=330/32$.

c) 8-benzyloxy-5-oxiranyl-1H-quinolin-2-one

A solution of 20 g (61 mmol) 8-benzyloxy-5-(2-chloro-1-hydroxy-ethyl)-1H-quinolin-2-one in 160 mL DMF is added dropwise at 0° C. to 35 mL of a 4 molar sodium hydroxide solution and then stirred for 2 hours at this temperature. The reaction mixture is combined with 1.5 L ice water, buffered by the addition of dry ice and extracted with ethyl acetate. The organic phases are dried with sodium sulphate, the solvent is distilled off and the residue is chromatographed over aluminium oxide (dichloromethane/ethyl acetate gradient). The fractions containing the product are evaporated down to 60 mL and then combined with petroleum ether, during which time a solid is precipitated, which is suction filtered and dried.

Yield: 9 g (48%); mass spectroscopy $[M+H]^+=294$.

Intermediate step 6:
7-benzyloxy-5-oxiranyl-1H-quinolin-2-one

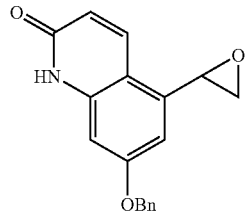

a) 2-acetyl-4-benzyloxy-6-nitro-phenyl trifluoromethanesulphonate 92.7 mL (660 mmol) triethylamine are added to 90 g (313 mmol) 1-(5-benzyloxy-2-hydroxy-3-nitro-phenyl)-ethanone in 940 mL dichloromethane at −10° C. Then a solution of 65 mL (394 mmol) trifluoromethanesulphonic anhydride and 40 mL dichloromethane is slowly added dropwise. After 15 minutes stirring at −5° C. the reaction is stopped by the careful addition of 400 mL ammonium chloride solution and 400 mL sodium hydrogen carbonate solution. The organic phase is separated off, dried with sodium sulphate and evaporated down. The residue is dissolved in 150 mL diethyl ether and then precipitated by the addition of 800 mL hexane. The solid is filtered off, suspended in a diethyl ether/hexane mixture and suction filtered again.

Yield: 118 g (90%); mass spectroscopy: $[M+H]^+=420$.

b) methyl 3-(2-acetyl-4-benzyloxy-6-nitro-phenyl)-acrylate 5.88 g (6.42 mmol) tris-(dibenzylideneacetone)-dipalladium, 3.50 g (12.01 mmol) tri-tert-butylphosphonium tetrafluoroborate, 81.2 mL (371 mmol) dicyclohexylmethylamine, 105.8 g (286 mmol) tetrabutylammonium iodide and 32.6 mL (362 mmol) methyl acrylate are added to a solution of 100 g (238 mmol) 2-acetyl-4-benzyloxy-6-nitro-phenyl trifluoromethanesulphonate in 360 mL dioxane. The reaction mixture is stirred for 2 hours at 80° C. under a nitrogen atmosphere and then combined with 2 L diethyl ether and 500 g silica gel. After 10 minutes the silica gel is suction filtered, while again being washed repeatedly with diethyl ether. The combined organic phases are washed successively with 1 N hydrochloric acid, sodium carbonate solution and sodium chloride solution. The solvent is distilled off, the residue recrystallised from ethanol and the solid is filtered off and washed with ethanol. Yield: 32.2 g (38%); mass spectroscopy: $[M+H]^+=356$.

c) 5-acetyl-7-benzyloxy-3,4-dihydro-1H-quinolin-2-one 5.0 g (14.07 mmol) methyl 3-(2-acetyl-4-benzyloxy-6-nitro-phenyl)-acrylate are combined with 100 mL ethanol and hydrogenated with Raney nickel as catalyst at 4 bar. The catalyst is separated off and the filtrate is acidified with 15 mL 2 N hydrochloric acid. The product that crystallises out is suction filtered and dried.

Yield: 1.0 g (24%); mass spectroscopy: $[M+H]^+=296$.

d) 5-acetyl-7-benzyloxy-1H-quinolin-2-one 13.0 g (44 mmol) 5-acetyl-7-benzyloxy-3,4-dihydro-1H-quinolin-2-one are suspended in 130 mL dioxane and combined with 15.0 g (66 mmol) 2,3-dichloro-5,6-dicyanobenzoquinone. The mixture is refluxed for 30 minutes, cooled to ambient temperature and stirred for a further 2 hours. The solid is filtered off, washed with dioxane and dissolved in 600 mL dichloromethane/methanol (9:1). The solution is washed with sodium hydrogen carbonate solution, dried with sodium sulphate and evaporated down. Then the residue is suspended in methanol, filtered and dried.

Yield: 8.3 g (64%); mass spectroscopy: [M+H]$^+$=294.

e) 7-benzyloxy-5-(2-chloro-acetyl)-1H-quinolin-2-one 7.0 g (23.9 mmol) 5-acetyl-7-benzyloxy-1H-quinolin-2-one and 19.0 g (54.6 mmol) benzyltrimethylammonium dichloriodate are stirred in 43 mL acetic acid, 7 mL water and 147 mL dichloroethane at 65° C. After 4.5 hours the reaction is stopped by the addition of 400 mL sodium carbonate solution and 50 mL 5% sodium bisulphite solution. The insoluble constituents are suction filtered, washed with water and dried.

Yield: 6.0 g (77%); mass spectroscopy: [M+H]$^+$=328.

f) 7-benzyloxy-5-oxiranyl-1H-quinolin-2-one 6.0 g (18.3 mmol) 7-benzyloxy-5-(2-chloro-acetyl)-1H-quinolin-2-one are placed in 150 mL tetrahydrofuran and at 0 to 5° C. combined with 434 mg (819.9 mmol) lithium borohydride. The mixture is stirred for 30 minutes, then 43 mL of a 2.5 molar sodium hydroxide solution are added and the mixture is stirred for a further 4 hours with heating to ambient temperature. The mixture is combined with sodium chloride solution, filtered and extracted repeatedly with ethyl acetate/tetrahydrofuran (1:1). The solid filtered off and the organic phases are combined and freed from the solvent. The residue is suspended in methanol, suction filtered and dried. Yield 4.8 g (89%); mass spectroscopy: [M+H]+=294.

Synthesis of the Final Compounds

EXAMPLE 1

8-hydroxy-5-{1-hydroxy-2-[2-(4-methoxy-phenyl)-1,1-dimethyl-ethylamino]-ethyl}-1H-quinolin-2-one

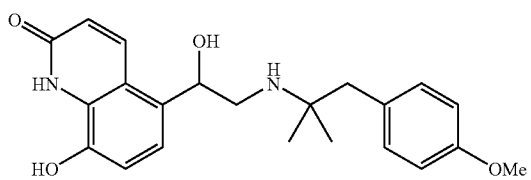

a) 8-benzyloxy-5-{1-hydroxy-2-[2-(4-methoxy-phenyl)-1,1-dimethyl-ethylamino]-ethyl}-1H-quinolin-2-one 587 mg (2 mmol) 8-benzyloxy-5-oxiranyl-1H-quinolin-2-one and 358 mg (2 mmol) 2-(4-methoxy-phenyl)-1,1-dimethyl-ethylamine are stirred in 5 mL n-butanol for 6 hours at 140° C. Then the solvent is distilled off and the residue is purified by chromatography (reverse phase; water/acetonitrile gradient).

Yield: 306 mg (32%); mass spectroscopy [M+H]$^+$=473.

b) 8-hydroxy-5-{1-hydroxy-2-[2-(4-methoxy-phenyl)-1,1-dimethyl-ethylamino]-ethyl}-1H-quinolin-2-one 306 mg (0.6 mmol) 8-benzyloxy-5-{1-hydroxy-2-[2-(4-methoxy-phenyl)-1,1-dimethyl-ethylamino]-ethyl}-1H-quinolin-2-one are dissolved in 10 mL methanol and hydrogenated with palladium on charcoal as catalyst at ambient temperature and normal pressure. Then the catalyst is separated off and the filtrate is freed from the solvent.

Yield: 145 mg (59%); mass spectroscopy [M+H]$^+$=389.

EXAMPLE 2

5-[2-[2-(2,4-difluoro-phenyl)-1-dimethyl-ethylamino]-1-hydroxy-ethyl]-8-hydroxy-3,4-dihydro-1H-quinolin-2-one

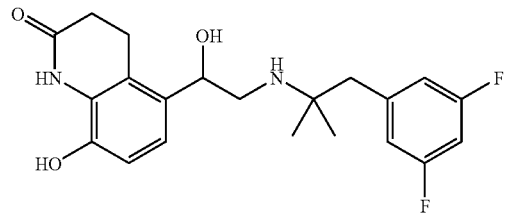

a) 8-benzyloxy-5-{2-[2-(2,4-difluoro-phenyl)-1,1-dimethyl-ethylamino]-1-hydroxy-ethyl}-1H-quinolin-2-one 587 mg (2 mmol) 8-benzyloxy-5-oxiranyl-1H-quinolin-2-one and 555 mg (3 mmol) 2-(2,4-difluoro-phenyl)-1,1-dimethyl-ethylamine are reacted and worked up as described for Example 1a). Yield: 220 mg (23%); mass spectroscopy [M+H]$^+$=479.

b) 5-{2-[2-(2,4-difluoro-phenyl)-1,1-dimethyl-ethylamino]-1-hydroxy-ethyl}-8-hydroxy-3,4-dihydro-1H-quinolin-2-one A solution of 220 mg (0.5 mmol) 8-benzyloxy-5-{2-[2-(2,4-difluoro-phenyl)-1,1-dimethyl-ethylamino]-1-hydroxy-ethyl}-1H-quinolin-2-one in 10 mL methanol is hydrogenated in the presence of palladium on charcoal at ambient temperature and normal pressure. Then the catalyst is separated off, the filtrate is evaporated down and the residue is chromatographed (reverse phase; water/acetonitrile gradient).

Yield: 56 mg (31%); mass spectroscopy [M+H]$^+$=391.

The following compounds (Examples 3 to 5, 7 and 8) may also be obtained analogously to to the examples of synthesis given above:

EXAMPLE 3

8-hydroxy-5-{1-hydroxy-2-[2-(4-hydroxy-phenyl)-1,1-dimethyl-ethylamino]-ethyl}-1H-quinolin-2-one

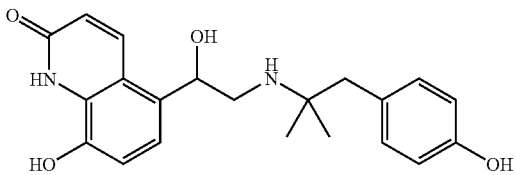

EXAMPLE 4

5-[2-{2-(4-fluoro-phenyl)-1,1-dimethyl-ethylamino]-1-hydroxy-ethyl}-8-hydroxy-3,4-dihydro-1H-quinolin-2-one

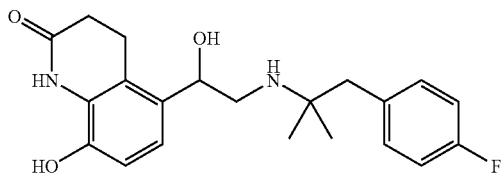

EXAMPLE 5

7-hydroxy-5-{1-hydroxy-2-[2-(4-methoxy-phenyl)-1,1-dimethyl-ethylamino]-ethyl}-1H-quinolin-2-one

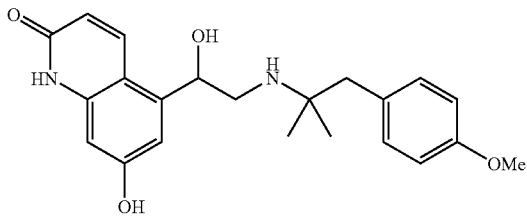

a) 7-benzyloxy-5-{1-hydroxy-2-[2-(4-methoxy-phenyl)-1,1-dimethyl-ethylamino]-ethyl}-1H-quinolin-2-one 150 mg (0.51 mmol) 7-benzyloxy-5-oxiranyl-1H-quinolin-2-one and 208 mg (1.2 mmol) 2-(4-methoxy-phenyl)-1,1-dimethyl-ethylamine are combined with 1 mL isopropanol and irradiated with microwaves for a total of 1 hour at 135° C. Then the reaction mixture is combined with ethyl acetate and 0.5 molar tartaric acid, whereupon a precipitate is formed. The organic phase is discarded and the solid and the aqueous phase are extracted with dichloromethane/methanol. The combined organic phases are evaporated down and combined with 8 mL ethyl acetate. The insoluble solid is suction filtered and dried. Yield: 130 mg (54%).

b) 7-hydroxy-5-{1-hydroxy-2-[2-(4-methoxy-phenyl)-1,1-dimethyl-ethylamino]-ethyl}-1H-quinolin-2-one 128 mg (0.27 mmol) 7-benzyloxy-5-{1-hydroxy-2-[2-(4-methoxy-phenyl)-1,1-dimethyl-ethylamino]-ethyl}-1H-quinolin-2-one are dissolved in 12 mL methanol and hydrogenated using palladium on charcoal as catalyst. The reaction mixture is filtered through Celite, eluted with methanol and the filtrate is freed from the solvent. Yield: 65 mg (63%); $R_f$=0.25 (silica gel, dichloromethane/methanol/ammonia=18:2:1).

EXAMPLE 6

5-{2-[2-(3,5-difluoro-phenyl)-1,1-dimethyl-ethylamino]-1-hydroxy-ethyl}-7-hydroxy-1H-quinolin-2-one

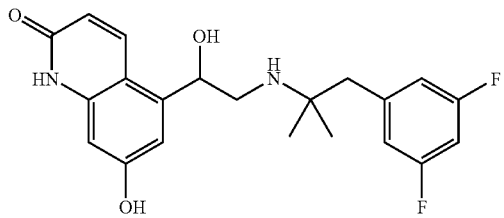

EXAMPLE 7

7-hydroxy-5-{1-hydroxy-2-[2-(4-methoxy-phenyl)-1,1-dimethyl-ethylamino]-ethyl}-3,4-dihydro-1H-quinolin-2-one

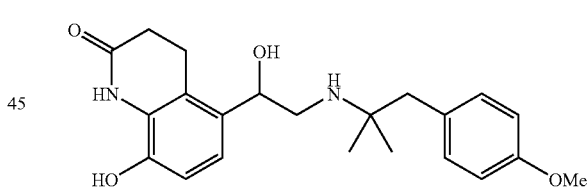

EXAMPLE 8

5-{2-[2-(4-ethoxy-phenyl)-1,1-dimethyl-ethylamino]-1-hydroxy-ethyl}-7-hydroxy-3,4-dihydro-1H-quinolin-2-one

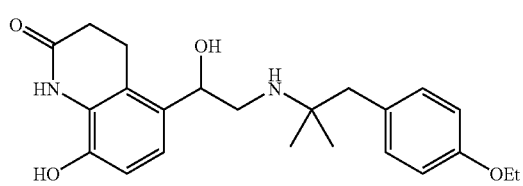

EXAMPLE 9

4-hydroxy-7-{1-hydroxy-2-[2-(4-methoxy-phenyl)-1,1-dimethyl-ethylamino]-ethyl}-3H-benzooxazol-2-one

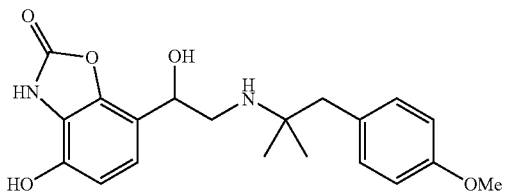

172 mg (0.5 mmol) 4-benzyloxy-7-(2-ethoxy-1,2-dihydroxy-ethyl)-3H-benzooxazol-2-one and 90 mg (0.5 mmol) 2-(4-methoxy-phenyl)-1,1-dimethyl-ethylamine in 8 mL ethanol are stirred for 90 minutes at 80° C. After cooling to ambient temperature 19 mg (0.5 mmol) sodium borohydride are added. The mixture is stirred for a further 2 hours, acidified with 1 N hydrochloric acid, stirred for 10 minutes and made alkaline with potassium carbonate solution. The mixture is combined with 40 mL ethyl acetate and filtered through kieselguhr. The filtrate is evaporated down and the residue purified by chromatography (reverse phase, acetonitrile/water gradient with 0.1% trifluoroacetic acid). The benzylether thus obtained is dissolved in 5 mL ethanol and hydrogenated in the presence of palladium on charcoal (10%) at 2.5 bar hydrogen pressure. Then the catalyst is separated off and the filtrate is freed from solvents. Yield: 20 mg (8%, trifluoroacetate), mass spectroscopy $[M+H]^+=373$.

EXAMPLE 10

4-hydroxy-7-{1-hydroxy-2-[2-(4-hydroxy-phenyl)-1,1-dimethyl-ethylamino]-ethyl}-3H-benzoxazol-2-one

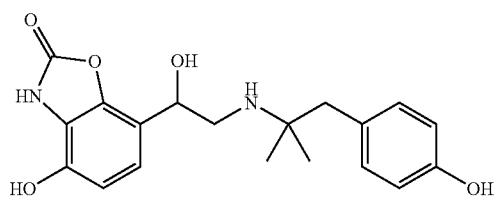

The compound is prepared analogously to Example 9 from 172 mg (0.5 mmol) 4-benzyloxy-7-(2-ethoxy-1,2-dihydroxy-ethyl)-3H-benzoxazol-2-one and 83 mg (0.5 mmol) 4-(2-amino-2-methyl-propyl)-phenol.

Yield: 29 mg (12%, trifluoroacetate); mass spectroscopy $[M+H]^+=359$.

EXAMPLE 11

5-hydroxy-8-{1-hydroxy-2-[2-(4-hydroxy-phenyl)-1,1-dimethyl-ethylamino]-ethyl}-2,2-dimethyl-4H-benzo[1,4]oxazin-3-one

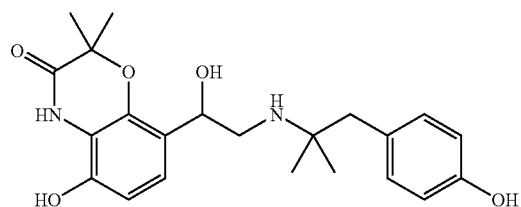

EXAMPLE 12

5-hydroxy-7-{1-hydroxy-2-[2-(4-methoxy-phenyl)-1,1-dimethyl-ethylamino]-ethyl}-3H-benzoxazol-2-one

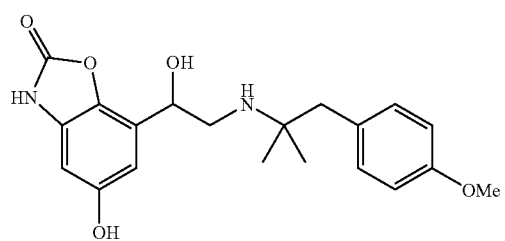

Obtained from 172 mg (0.5 mmol) 5-benzyloxy-7-(2-ethoxy-2-hydroxy-acetyl)-3H-benzoxazol-2-one and 90 mg (0.5 mmol) 2-(4-methoxy-phenyl)-1,1-dimethyl-ethylamine analogously to the method described for Example 9.

Yield: 88 mg (36%, trifluoroacetate); mass spectroscopy $[M+H]^+=373$.

EXAMPLE 13

7-{2-[2-(4-ethoxy-phenyl)-1,1-dimethyl-ethylamino]-1-hydroxy-ethyl}-5-hydroxy-3H-benzoxazol-2-one

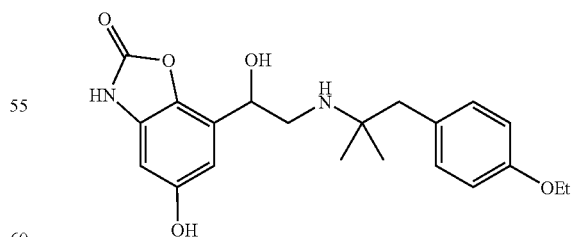

Prepared from 172 mg (0.5 mmol) 5-benzyloxy-7-(2-ethoxy-2-hydroxy-acetyl)-3H-benzoxazol-2-one and 97 mg (0.5 mmol) 2-(4-ethoxy-phenyl)-1,1-dimethyl-ethylamine analogously to the method described for Example 9.

Yield: 41 mg (16%, trifluoroacetate); mass spectroscopy $[M+H]^+=387$.

EXAMPLE 14

6-hydroxy-8-{1-hydroxy-2-[2-(4-methoxy-phenyl)-1,1-dimethyl-ethylamino]-ethyl}-2,2-dimethyl-4H-benzo[1,4]oxazin-3-one

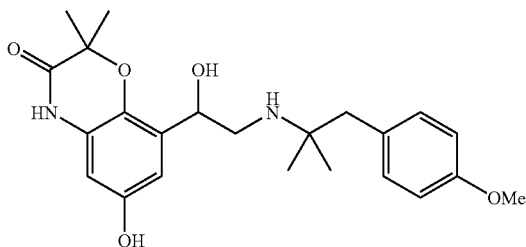

385 mg (1 mmol) 6-benzyloxy-8-(2-ethoxy-2-hydroxy-acetyl)-2,2-dimethyl-4H-benzo[1,4]oxazin-3-on and 179 mg (1 mmol) 2-(4-methoxy-phenyl)-1,1-dimethyl-ethylamine are stirred in 5 mL tetrahydrofuran for 30 minutes at 50° C. The mixture is cooled to 0° C. and combined with 1.5 mL of a 2 molar solution of lithium borohydride in tetrahydrofuran. The mixture is stirred for 30 minutes at 0° C. and then 10 mL dichloromethane and 3 mL water are added. The mixture is stirred for one hour at ambient temperature and filtered through kieselguhr, eluting with dichloromethane. The filtrate is evaporated down and the residue is purified by chromatography (reverse phase, acetonitrile/water gradient with 0.1% trifluoroacetic acid). The benzylether thus obtained is dissolved in methanol and hydrogenated with palladium on charcoal (10%) as catalyst at 2.5 bar hydrogen pressure and ambient temperature. The catalyst is separated off, the solvent is distilled off and the residue is purified by chromatography.

Yield: 144 mg (27%, trifluoroacetate); mass spectroscopy [M+H]⁺=415.

EXAMPLE 15

8-{2-[2-(4-fluoro-phenyl)-1,1-dimethyl-ethylamino]-1-hydroxy-ethyl}-6-hydroxy-2,2-dimethyl-4H-benzo[1,4]oxazin-3-one

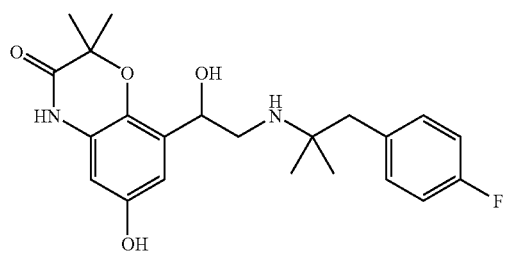

a) 6-benzyloxy-8-{2-[2-(4-fluoro-phenyl)-1,1-dimethyl-ethylamino]-1-hydroxy-ethyl}-2,2-dimethyl-4H-benzo[1,4]oxazin-3-one 385 mg (1 mmol) 6-benzyloxy-8-(2-ethoxy-2-hydroxy-acetyl)-2,2-dimethyl-4H-benzo[1,4]oxazin-3-one and 167 mg (1 mmol) 2-(4-fluoro-phenyl)-1,1-dimethyl-ethylamine are reacted and worked up analogously to Example 14. However, the resulting benzylether is chromatographed on a silica gel column (dichloromethane/methanol gradient).

Yield: 290 mg (59%); mass spectroscopy [M+H]⁺=493.

b) 8-{2-[2-(4-fluoro-phenyl)-1,1-dimethyl-ethylamino]-1-hydroxy-ethyl}-6-hydroxy-2,2-dimethyl-4H-benzo[1,4]oxazin-3-one 280 mg (0.57 mmol) 6-benzyloxy-8-{2-[2-(4-fluoro-phenyl)-1,1-dimethyl-ethylamino]-1-hydroxy-ethyl}-2,2-dimethyl-4H-benzo[1,4]oxazin-3-one are dissolved in 7 mL methanol and hydrogenated with palladium on charcoal (10%) at ambient temperature. Then the catalyst is separated off and the filtrate is freed from the solvent. The residue is dissolved in dichloromethane and precipitated by the addition of methanol/water. White solid.

Yield: 90 mg (39%); mass spectroscopy [M−H]⁺=401.

EXAMPLE 16

5-hydroxy-8-{1-hydroxy-2-[2-(4-methoxy-phenyl)-1,1-dimethyl-ethylamino]-ethyl}-2,2-dimethyl-4H-benzo[1,4]oxazin-3-one

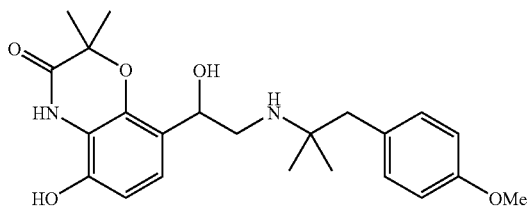

a) 5-benzyloxy-8-{1-hydroxy-2-[2-(4-methoxy-phenyl)-1,1-dimethyl-ethylimino]-ethyl}-2,2-dimethyl-4H-benzo[1,4]oxazin-3-one 10.1 g (26 mmol) 5-benzyloxy-8-(2-ethoxy-2-hydroxy-acetyl)-2,2-dimethyl-4H-benzo[1,4]oxazin-3-one and 4 g (22 mmol) 2-(4-methoxy-phenyl)-1,1-dimethyl-ethylamine are stirred in 100 ml of ethanol for 2 hours at 60 to 70° C. After some of the solvent has been distilled off a solid is precipitated out during cooling, and this is suction filtered and washed with ethanol and diethyl ether.

Yield: 8.7 g (78%); melting range=138-140° C.

b) 5-benzyloxy-8-{1-hydroxy-2-[2-(4-methoxy-phenyl)-1,1-dimethyl-ethylamino]-ethyl}-2,2-dimethyl-4H-benzo[1,4]oxazin-3-one 0.6 g sodium borohydride are added at ambient temperature to a solution of 8.6 g (17 mmol) 5-benzyloxy-8-{1-hydroxy-2-[2-(4-methoxy-phenyl)-1,1-dimethyl-ethylimino]-ethyl}-2,2-dimethyl-4H-benzo[1,4]oxazin-3-one in 80 mL ethanol and the mixture is stirred for one hour. The reaction mixture is combined with 20 mL acetone, stirred for 30 minutes, diluted with 50 ml of water and acidified with glacial acetic acid. After the organic solvents have been distilled off ethyl acetate is added to the aqueous residue. It is acidified with conc. hydrochloric acid and diluted with diethyl ether. The product precipitated as the hydrochloride is suction filtered and washed with acetone and diethyl ether. Yield: 8.4 g (91%, hydrochloride); melting range=215-218° C.

c) 5-hydroxy-8-{1-hydroxy-2-[2-(4-methoxy-phenyl)-1,1-dimethyl-ethylamino]-ethyl}-2,2-dimethyl-4H-benzo[1,4]oxazin-3-one 7.3 g (14 mmol) 5-benzyloxy-8-{1-hydroxy-2-[2-(4-methoxy-phenyl)-1,1-dimethyl-ethylamino]-ethyl}-2,2-dimethyl-4H-benzo[1,4]oxazin-3-one hydrochloride are hydrogenated in 125 mL methanol with palladium on charcoal as catalyst. The catalyst is separated off and the solvent is substantially distilled off. Acetone is added, the precipitated solid is filtered off and washed with acetone and diethyl ether.

Yield: 5.4 g (89%, hydrochloride); melting range=200° C. (decomposition).

Suitable preparations for administering the compounds of formula 1 include tablets, capsules, suppositories, solutions, powders, etc. The proportion of pharmaceutically active compound or compounds should be in the range from 0.05 to 90% by weight, preferably 0.1 to 50% by weight of the total composition. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, arabic gum, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations of active substances according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

When the compounds of formula 1 are used, as preferred according to the invention, for the treatment of respiratory complaints, it is particularly preferable to use preparations or pharmaceutical formulations that can be administered by inhalation. Suitable formulations for inhalation include inhalable powders, propellant-driven metered—dose aerosols or propellant-free inhalable solutions. Within the scope of the present invention the term propellant-free inhalable solutions also includes concentrates or sterile ready-to-use inhalable solutions. The formulations which may be used within the scope of the present invention are described in detail in the next part of the specification.

The inhalable powders which may be used according to the invention may contain 1 either on their own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 and 150 µm, most preferably between 15 and 80 µm. In some cases it may seem appropriate to add finer excipient fractions with an average particle size of 1 to 9 µm to the excipient mentioned above. These finer excipients are also selected from the group of possible excipients listed hereinbefore. Finally, in order to prepare the inhalable powders according to the invention, micronised active substance 1, preferably with an average particle size of 0.5 to 10 µm, more preferably from 1 to 5 µm, is added to the excipient mixture. Processes for producing the inhalable powders according to the invention by grinding and micronising and finally mixing the ingredients together are known from the prior art.

The inhalable powders according to the invention may be administered using inhalers known from the prior art.

The inhalation aerosols containing propellant gas according to the invention may contain the compounds 1 dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The above-mentioned propellant gases may be used on their own or in admixture. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabiliser or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation the compounds of formula 1 are characterised by a high potency even at doses in the µg range. The compounds of formula 1 may also be used effectively above the µg range. The dosage may then be in the milligram range, for example.

In another aspect the present invention relates to the above-mentioned pharmaceutical formulations, characterised in that they contain a compound of formula 1, as such, particularly preferably the above-mentioned pharmaceutical formulations for use by inhalation.

The following formulation examples illustrate the present invention without restricting its scope:

A)

| Ampoule solution | |
|---|---|
| active substance of formula 1 | 25 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

B)

| Metered-dose aerosol (suspension) | |
|---|---|
| active substance of formula 1 | 0.03 wt. % |
| sorbitolan trioleate | 0.6 wt. % |
| HFA134A:HFA227 2:1 | 99.37 wt. % |

The suspension is poured into a conventional aerosol container with metering valve. Preferably 50 μl suspension are delivered in each puff. The active substance may if desired also be delivered in higher doses.

C)

| Metered-dose aerosol (solution) | |
|---|---|
| active substance of formula 1 | 0.03 wt. % |
| ethanol abs. | 20 wt. % |
| aqueous HCl 0.01 mol/1 | 2.0 wt. % |
| HFA134A | 77.97 wt. % |

The solution is prepared in the conventional manner by mixing the individual constituents.

D)

| Inhalable powder | |
|---|---|
| active substance of formula 1 | 80 μg |
| lactose monohydrate | ad 10 mg |

The inhalable powder is prepared in the conventional manner by mixing the individual constituents.

What is claimed is:

1. A compound of formula 1

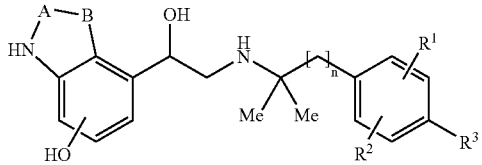

wherein
n denotes 1 or 2;
A denotes a divalent group selected from among —(C=O)—, —S(=O)—, —S(=O)$_2$— and —C($R^4R^5$)—;
B denotes a divalent group selected from among —O—, —$NR^6$—, —$CH_2$—, —S—$CR^7R^8$—, —$NR^6$—$CR^7R^8$—, —$CH_2$—$CR^7R^8$—, and —O—$CR^9R^{10}$—;
$R^1$ and $R^2$ which may be identical or different, denote hydrogen, $C_1$-$C_4$-alkyl, halogen, OH or —O—$C_1$-$C_4$-alkyl;
$R^3$ denotes hydrogen, $C_1$-$C_4$-alkyl, OH, fluorine, chlorine, bromine, —O—$C_1$-$C_4$-alkyl, —COOH, —COO—$C_1$-$C_4$-alkyl, —O—$C_1$-$C_4$-alkylene-COOH or —O—$C_1$-$C^4$-alkylene-CO—O—$C_1$-$C_4$-alkyl, provided that $R^3$ does not denote hydrogen or fluorine when B is —O— or —O—$CR^9R^{10}$—, and provided that $R^3$ does not denote hydrogen when B is —$CH_2$—$CH_2$—;
$R^4$ and $R^5$ which may be identical or different, denote hydrogen, $C_1$-$C_4$-alkyl, OH, halogen, —O—$C_1$-$C_4$-alkyl, —COOH or —COO—$C_1$-$C_4$-alkyl;
$R^6$ denotes hydrogen or $C_1$-$C_4$-alkyl;
$R^7$ and $R^8$ which may be identical or different, denote hydrogen or $C_1$-$C_4$-alkyl,
$R^9$ and $R^{10}$ which may be identical or different, denote $C_1$-$C_4$-alkyl,
the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

2. The compound of formula 1 according to claim 1, wherein
n denotes 1 or 2;
A denotes a divalent group selected from among —(C=O)—, —S(=O)$_2$— and —C($R^4R^5$)—;
B denotes a divalent group selected from among —O—, —$NR^6$—, —$CH_2$—, —S—$CR^7R^8$—, —$NR^6$—$CR^7R^8$—, —$CH_2$—$CR^7R^8$— and —O—$CR^9R^{10}$—;
$R^1$ and $R^2$ which may be identical or different, denote hydrogen, methyl, ethyl, propyl, fluorine, chlorine, bromine, OH, methoxy or ethoxy;
$R^3$ denotes hydrogen, methyl, ethyl, propyl, fluorine, chlorine, bromine, OH, methoxy, ethoxy, —COOH, —COOmethyl, —COOethyl, —O—$CH_2$—COOH, —O—$CH_2$—COO-methyl, —O—$CH_2$—COO-ethyl, —O—$CH_2$—$CH_2$—COOH, —O—$CH_2$—$CH_2$—COO-methyl, —O—$CH_2$—$CH_2$—COO-ethyl, —O—$CH_2$—$CH_2$—$CH_2$—COOH, —O—$CH_2$—$CH_2$—$CH_2$—COO-methyl or —O—$CH_2$—$CH_2$—$CH_2$—COO-ethyl, provided that $R^3$ not denote hydrogen or fluorine when B is —O— or —O—$CR^9R^{10}$—, and provided that $R^3$ does not denote hydrogen when B is —$CH_2$—$CH_2$—;
$R^4$ and $R^5$ which may be identical or different, denote hydrogen, methyl, ethyl, OH, fluorine, chlorine, —COOH, —COOmethyl or —COOethyl;
$R^6$ denotes hydrogen, methyl, ethyl or propyl;
$R^7$ and $R^8$ which may be identical or different, denote hydrogen, methyl, ethyl or propyl,
$R^9$ and $R^{10}$ which may be identical or different, denote methyl, ethyl or propyl,
the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

3. The compound of formula 1 according to claim 1, wherein
n denotes 1 or 2;
A denotes a divalent group selected from among —(C=O)—, —S(=O)$_2$— and —C($R^4R^5$)—;
B denotes a divalent group selected from among —O—, —$NR^6$—, —$CH_2$—, —S—$CR^7R^8$—, —$NR^6$—$CR^7R^8$—, —$CH_2$—$CR^7R^8$—, and —O—$CR^9R^{10}$—;
$R^1$ and $R^2$ which may be identical or different, denote hydrogen, methyl, ethyl, fluorine, chlorine, OH, methoxy or ethoxy;
$R^3$ denotes hydrogen, methyl, ethyl, fluorine, chlorine, OH, methoxy, ethoxy, —COOH, —COOmethyl, —COOethyl, —O—$CH_2$—COOH, —O—$CH_2$—COO-methyl, —O—$CH_2$—COO-ethyl, —O—$CH_2$—$CH_2$—COOH, —O—$CH_2$—$CH_2$—COO-methyl, or —O—$CH_2$—$CH_2$—COO-ethyl, provided that $R^3$ does not denote hydrogen or fluorine when B is —O— or —O—$CR^9R^{10}$—, and provided that $R^3$ does not denote hydrogen when B is —$CH_2$—$CH_2$—;

$R^4$ and $R^5$ which may be identical or different, denote hydrogen, methyl, ethyl, —COOH, —COOmethyl or —COOethyl;

$R^6$ denotes hydrogen, methyl or ethyl;

$R^7$ and $R^8$ which may be identical or different, denote hydrogen, methyl or ethyl, $R^9$ and $R^{10}$ which may be identical or different, denote methyl or ethyl, the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

4. The compound of formula 1 according to claim 1, wherein n denotes 1 or 2;

A denotes a divalent group selected from among —(C=O)—, —S(=O)$_2$— and —C($R^4R^5$)—;

B denotes a divalent group selected from among —O—, —NH—, —$CH_2$—, —S—$CH_2$—, —NH—$CH_2$—, —$CH_2$—$CH_2$— and —O—$CR^9R^{10}$—;

$R^1$ and $R^2$ which may be identical or different, denote hydrogen, methyl, ethyl, fluorine, chlorine, OH, methoxy or ethoxy;

$R^3$ denotes hydrogen, methyl, ethyl, fluorine, chlorine, OH, methoxy, ethoxy, —COOH, —COOmethyl, —COOethyl, —O—$CH_2$—COOH, —O—$CH_2$—COO-methyl, —O—$CH_2$—COO-ethyl, —O—$CH_2$—$CH_2$—COOH, —O—$CH_2$—$CH_2$—COO-methyl or —O—$CH_2$—$CH_2$—COO-ethyl, provided that $R^3$ does not denote hydrogen or fluorine when B is —O— or —O—$CR^9R^{10}$—, and provided that $R^3$ does not denote hydrogen when B is —$CH_2$—$CH_2$—;

$R^4$ and $R^5$ which may be identical or different, denote hydrogen, methyl, ethyl, —COOH, —COOmethyl or —COOethyl;

$R^9$ and $R^{10}$ which may be identical or different, denote methyl or ethyl, the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

5. The compound of formula 1 according to claim 1, wherein n denotes 1 or 2;

A denotes a divalent group selected from among —(C=O)— and —S(=O)$_2$—;

B denotes a divalent group selected from among —O—, —NH—, —$CH_2$—, —S—$CH_2$—, —NH—$CH_2$—, —$CH_2$—$CH_2$— and —O—$CR^9R^{10}$—;

$R^1$ and $R^2$ which may be identical or different, denote hydrogen, methyl, ethyl, fluorine, chlorine, OH, methoxy or ethoxy;

$R^3$ denotes hydrogen, methyl, ethyl, fluorine, chlorine, OH, methoxy, ethoxy, —COOH, —COOmethyl, —COOethyl, —O—$CH_2$—COOH, —O—$CH_2$—COO-methyl, —O—$CH_2$—COO-ethyl, —O—$CH_2$—$CH_2$—COOH, —O—$CH_2$—$CH_2$—COO-methyl or —O—$CH_2$—$CH_2$—COO-ethyl, provided that $R^3$ does not denote hydrogen or fluorine when B is —O— or —O—$CR^9R^{10}$—, and provided that $R^3$ does not denote hydrogen when B is —$CH_2$—$CH_2$—;

$R^9$ and $R^{10}$ which may be identical or different, denote methyl or ethyl, the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

6. The compound of formula 1 according to claim 1, wherein $R^1$ and $R^2$ which may be identical or different, denote hydrogen, methyl, ethyl, fluorine, chlorine, OH, methoxy or ethoxy;

$R^3$ denotes hydrogen,

B denotes a divalent group selected from among —$NR^6$—, —$CH_2$—, —S—$CR^7R^8$—, and —$NR^6$—$CR^7R^8$—, the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

7. The compound of formula 1 according to claim 1, wherein $R^1$ and $R^2$ which may be identical or different, denote hydrogen, methyl, fluorine, chlorine or methoxy;

$R^3$ denote hydrogen, methyl, fluorine, chlorine or methoxy, provided that $R^3$ does not denote hydrogen or fluorine when B is —O— or —O—$CR^9R^{10}$—, and provided that $R^3$ does not denote hydrogen when B is —$CH_2$—$CH_2$—;

the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

8. The compound of formula 1 according to claim 1, wherein $R^3$ denotes methyl, ethyl, fluorine, chlorine, OH, methoxy, ethoxy, —COOH, —COOmethyl, —COOethyl, —O—$CH_2$—COOH, —O—$CH_2$—COOmethyl, —O—$CH_2$—COOethyl, —O—$CH_2$—$CH_2$—COOH, —O—$CH_2$—$CH_2$—COOmethyl or —O—$CH_2$—$CH_2$—COOethyl, provided that $R^3$ does not denote hydrogen or fluorine when B is —O— or —O—$CR^9R^{10}$—;

the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

9. The compound of formula 1 according to claim 1, wherein $R^3$ denotes methyl, ethyl, OH, methoxy, ethoxy, —O—$CH_2$—COOH, —O—$CH_2$—COOmethyl or —O—$CH_2$—COOethyl, the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

10. A compounds of formula 1 according to claim 1, wherein the compound is in the form of one of the acid addition salts thereof with a pharmacologically acceptable acid which is selected from among hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate.

11. The compound of formula 1 according to claim 1, wherein the compound is in the form of an R-enantiomers of general formula R-1

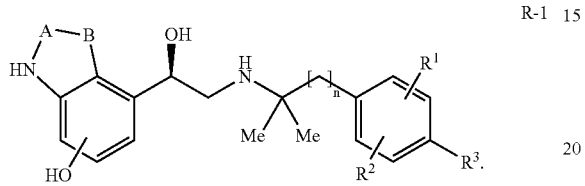

12. A pharmaceutical composition comprising a compound of formula 1 according to claim 1 and a pharmaceutically acceptable carrier or excipient.

13. A method of treating a respiratory disease selected from obstructive pulmonary diseases, pulmonary emphysemas, restrictive pulmonary diseases, interstitial pulmonary diseases, cystic fibrosis, muscoviscidosis, bronchitis, bronchiectasis, adult respiratory distress syndrome, and pulmonary oedemas comprising administering to a patient in need thereof a therapeutically effective amount of a compound of formula 1 according to claim 1.

14. The method of claim 13, wherein the disease is asthma or COPD.

15. A compound of formula 1 according to claim 1, wherein the compound is:
   5-{2-[2-(2,4-difluoro-phenyl)-1,1-dimethyl-ethylamino]-1-hydroxy-ethyl}-8-hydroxy-3,4-dihydro-1H-quinolin-2-one;
   5-{2-[2-(4-fluoro-phenyl)-1,1-dimethyl-ethylamino]-1-hydroxy-ethyl}-8-hydroxy-3,4-dihydro-1H-quinolin-2-one;
   7-hydroxy-5-{1-hydroxy-2-[2-(4-methoxy-phenyl)-1,1-dimethyl-ethylamino]-ethyl}-3,4-dihydro-1H-quinolin-2-one;
   5-{2-[2-(4-ethoxy-phenyl)-1,1-dimethyl-ethylamino]-1-hydroxy-ethyl}-7-hydroxy-3,4-dihydro-1H-quinolin-2-one;
   4-hydroxy-7-{1-hydroxy-2-[2-(4-methoxy-phenyl)-1,1-dimethyl-ethylamino]-ethyl}-3H-benzoxazol-2-one;
   4-hydroxy-7-{1-hydroxy-2-[2-(4-hydroxy-phenyl)-1,1-dimethyl-ethylamino]-ethyl}-3H-benzoxazol-2-one;
   5-hydroxy-8-{1-hydroxy-2-[2-(4-hydroxy-phenyl)-1,1-dimethyl-ethylamino]-ethyl}-2,2-dimethyl-4H-benzo[1,4]oxazin-3-one;
   5-hydroxy-7-{1-hydroxy-2-[2-(4-methoxy-phenyl)-1,1-dimethyl-ethylamino]-ethyl}-3H-benzoxazol-2-one;
   7-{2-[2-(4-ethoxy-phenyl)-1,1-dimethyl-ethylamino]-1-hydroxy-ethyl}-5-hydroxy 3H-benzoxazol-2-one;
   6-hydroxy-8-{1-hydroxy-2-[2-(4-methoxy-phenyl)-1,1-dimethyl-ethylamino]-ethyl}-2,2-dimethyl-4H-benzo[1,4]oxazin-3-one;
   8-{2-[2-(4-fluoro-phenyl)-1,1-dimethyl-ethylamino]-1-hydroxy-ethyl}-6-hydroxy 2,2-dimethyl-4H-benzo[1,4]oxazin-3-one and 5-hydroxy-8-{1-hydroxy-2-[2-(4-methoxy-phenyl)-1,1-dimethyl-ethylamino]-ethyl}-2,2-dimethyl-4H-benzo[1,4]oxazin-3-one,
   the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

16. A compound of formula 1 according to claim 1, wherein the compound is:
   5-{2-[2-(2,4-difluoro-phenyl)-1,1-dimethyl-ethylamino]-1-hydroxy-ethyl}-8-hydroxy-3,4-dihydro-1H-quinolin-2-one;
   the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

17. A compound of formula 1 according to claim 1, wherein the compound is:
   5-{2-[2-(4-fluoro-phenyl)-1,1-dimethyl-ethylamino]-1-hydroxy-ethyl}-8-hydroxy-3,4-dihydro-1H-quinolin-2-one;
   the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

18. A compound of formula 1 according to claim 1, wherein the compound is:
   7-hydroxy-5-{1-hydroxy-2-[2-(4-methoxy-phenyl)-1,1-dimethyl-ethylamino]-ethyl}-3,4-dihydro-1H-quinolin-2-one;
   the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

19. A compound of formula 1 according to claim 1, wherein the compound is:
   5-{2-[2-(4-ethoxy-phenyl)-1,1-dimethyl-ethylamino]-1-hydroxy-ethyl}-7-hydroxy-3,4-dihydro-1H-quinolin-2-one;
   the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

20. A compound of formula 1 according to claim 1, wherein the compound is:
   4-hydroxy-7-{1-hydroxy-2-[2-(4-methoxy-phenyl)-1,1-dimethyl-ethylamino]-ethyl}-3H-benzoxazol-2-one;
   the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

21. A compound of formula 1 according to claim 1, wherein the compound is:
   4-hydroxy-7-{1-hydroxy-2-[2-(4-hydroxy-phenyl)-1,1-dimethyl-ethylamino]-ethyl}-3H-benzoxazol-2-one;

the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

22. A compound of formula 1 according to claim 1, wherein the compound is:

5-hydroxy-8-{1-hydroxy-2-[2-(4-hydroxy-phenyl)-1,1-dimethyl-ethylamino]-ethyl}-2,2-dimethyl-4H-benzo[1,4]oxazin-3-one;

the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

23. A compound of formula 1 according to claim 1, wherein the compound is:

5-hydroxy-7-{1-hydroxy-2-[2-(4-methoxy-phenyl)-1,1-dimethyl-ethylamino]-ethyl}-3H-benzoxazol-2-one;

the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

24. A compound of formula 1 according to claim 1, wherein the compound is:

7-{2-[2-(4-ethoxy-phenyl)-1,1-dimethyl-ethylamino]-1-hydroxy-ethyl}-5-hydroxy 3H-benzoxazol-2-one;

the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

25. A compound of formula 1 according to claim 1, wherein the compound is:

6-hydroxy-8-{1-hydroxy-2-[2-(4-methoxy-phenyl)-1,1-dimethyl-ethylamino]-ethyl}-2,2-dimethyl-4H-benzo[1,4]oxazin-3-one;

the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

26. A compound of formula 1 according to claim 1, wherein the compound is:

8-{2-[2-(4-fluoro-phenyl)-1,1-dimethyl-ethylamino]-1-hydroxy-ethyl}-6-hydroxy 2,2-dimethyl-4H-benzo[1,4]oxazin-3-one and the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

27. A compound of formula 1 according to claim 1, wherein the compound is:

5-hydroxy-8-{1-hydroxy-2-[2-(4-methoxy-phenyl)-1,1-dimethyl-ethylamino]-ethyl}-2,2-dimethyl-4H-benzo[1,4]oxazin-3-one, the compound being optionally in the form of the individual enantiomers, mixtures of the individual enantiomers or racemates, and optionally in the form of the acid addition salts thereof with pharmacologically acceptable acids, as well as optionally in the form of the solvates and/or hydrates thereof.

\* \* \* \* \*